United States Patent [19]

Schmalstieg et al.

[11] Patent Number: 5,747,628
[45] Date of Patent: May 5, 1998

[54] POLYISOCYANATES CONTAINING ETHER AND URETHANE GROUPS, A PROCESS FOR THEIR PREPARATION AND THEIR USE IN THE PRODUCTION OF POLYURETHANE LACQUERS

[75] Inventors: Lutz Schmalstieg, Köln; Hermann Gruber, Leverkusen; Bernd Riberi, Odenthal-Osenau; Klaus Nachtkamp, Düsseldorf, all of Germany

[73] Assignee: Bayer Aktiengesellschaft, Leverkusen, Germany

[21] Appl. No.: 984,596

[22] Filed: Dec. 2, 1992

[30] Foreign Application Priority Data

Dec. 10, 1991 [DE] Germany ............ 41 40 660.5

[51] Int. Cl.$^6$ ............ C08G 18/10; C08G 18/76; C07C 269/02; C07C 271/26
[52] U.S. Cl. ............ 528/60; 252/182.22; 528/65; 528/66; 528/67; 528/76; 528/77; 560/25; 560/26; 560/358; 560/360
[58] Field of Search ............ 528/60, 65, 66, 528/76, 77, 67; 560/25, 26, 358, 360; 252/182.22

[56] References Cited

U.S. PATENT DOCUMENTS

| | | | |
|---|---|---|---|
| 3,049,513 | 8/1962 | Damusis et al. | 528/66 |
| 3,183,112 | 5/1965 | Gemassmer | 106/316 |
| 3,268,488 | 8/1966 | Heiss | 528/77 |
| 3,384,624 | 5/1968 | Hess | 528/49 |
| 3,652,506 | 3/1972 | Gibier-Rambaud et al. | 528/77 |
| 3,723,394 | 3/1973 | Gibier-Rambaud et al. | 528/76 |
| 3,839,491 | 10/1974 | Gamero et al. | 528/77 |
| 3,992,316 | 11/1976 | Pedain et al. | 252/182 |
| 4,169,175 | 9/1979 | Marans et al. | 528/66 |
| 4,385,171 | 5/1983 | Schnabel et al. | 528/491 |
| 4,579,929 | 4/1986 | Kay et al. | 528/65 |
| 4,683,279 | 7/1987 | Milligan et al. | 528/76 |
| 4,906,720 | 3/1990 | Parfondry | 528/77 |
| 4,910,332 | 3/1990 | Kahl et al. | 560/351 |
| 5,051,152 | 9/1991 | Siuta et al. | 203/49 |
| 5,654,390 | 8/1997 | Gajewski et al. | 528/63 |

FOREIGN PATENT DOCUMENTS

| | | |
|---|---|---|
| 870400 | 3/1953 | Germany . |
| 953012 | 11/1956 | Germany . |
| 1090186 | 10/1960 | Germany . |
| 1090196 | 10/1960 | Germany . |
| 1458564 | 12/1976 | United Kingdom . |

*Primary Examiner*—Rabon Sergent
*Attorney, Agent, or Firm*—Joseph C. Gil; Lyndanne M. Whalen

[57] ABSTRACT

Polyisocyanates based on polyhydroxy polyethers and tolylene diisocyanate containing ether and urethane groups and having an isocyanate group content of from 11.8 to 14.4% by weight, an average isocyanate functionality of from 3.1 to 4.0 and a free tolylene diisocyanate content of less than 0.1% by weight are produced by reacting a polyhydroxy polyether having a molecular weight in the range of from about 350 to about 500 with excess quantities of tolylene diisocyanate and subsequently distilling the mixture to remove unreacted excess of the starting diisocyanate. These polyisocyanates are particularly useful in the production of polyurethane lacquers.

8 Claims, No Drawings

POLYISOCYANATES CONTAINING ETHER AND URETHANE GROUPS, A PROCESS FOR THEIR PREPARATION AND THEIR USE IN THE PRODUCTION OF POLYURETHANE LACQUERS

BACKGROUND OF THE INVENTION

This invention relates to polyisocyanates based on tolylene diisocyanate which contain ether and urethane groups, to a process for their preparation and to their use as polyisocyanate components in one-component and two-component polyurethane lacquers.

Urethane group-containing polyisocyanates obtained from low molecular weight polyhydric alcohols and tolylene diisocyanate are known and are described, for example, in German Patent Specifications Nos. 870,400, 953,012 and 1,090,196. Such products are of great importance in the field of polyurethane lacquers and coatings and for adhesives. Commercial products are currently produced by reacting polyhydric alcohols with an excess of tolylene diisocyanate of from 5 to 10 times the quantity of alcohol present and then removing the excess starting diisocyanate by distillation, preferably in a thin layer evaporator. Such processes are described, for example, in DE-PS 1,090,186 and U.S. Pat. No. 3,183,112. The polyisocyanates which are produced by these methods have, however, two basic disadvantages. First, when the polyisocyanate is used in combination with commercial polyols, the products have a relatively short processing time so that they cannot be optimally used in all fields of application. Secondly, the known products have a very high melt viscosity. Consequently, removal of the tolylene diisocyanate by distillation can only be carried out down to a residue of about 0.2% by weight. For reasons of hygiene in the work place, however, it is desirable to reduce the monomer content to less than 0.1% by weight.

Numerous chemical after-treatment methods for removing residual monomers have been described in the Patent literature (e.g. U.S. Pat. No. 3,384,624, DE-OS 2,414,413 and 2,414,391). Such methods of reduction in monomer content, however, require additional and hence expensive process steps which generally produce a pronounced change in the properties of the polyisocyanate. Thus, chemical after-treatment methods are not employed in the industrial production of polyisocyanates.

SUMMARY OF THE INVENTION

It is therefore an object of the present invention to provide urethane group-containing polyisocyanates based on tolylene diisocyanate which have a low monomer content and which make longer processing times possible.

It is also an object of the present invention to provide a process for the production of such urethane group-containing polyisocyanates.

These and other objects which will be apparent to those skilled in the art are accomplished by reacting an organic polyhydroxy polyether having a molecular weight of from about 350 to about 500 with an excess of tolylene diisocyanate and distilling the reaction mixture to remove unreacted excess tolylene diisocyanate until the residual diisocyanate content is less than 0.1% by weight. The polyisocyanates thus obtained are characterized by an NCO content of from about 11.8 to about 14.4% by weight, an average NCO functionality of from about 3.1 to about 4.0 and a free tolylene diisocyanate content of less than about 0.1%.

DETAILED DESCRIPTION OF THE INVENTION

The present invention is based on the surprising observation that adducts of tolylene diisocyanate and certain polyether alcohols, in particular polyether triols, have a reduced reactivity with polyhydroxy compounds and at the same time a low melt viscosity so that monomers can easily be removed by distillation down to a residue of less than 0.1% by weight.

The present invention relates to polyisocyanates containing ether groups and urethane groups, based on polyhydroxy polyethers and tolylene diisocyanate, characterized by an isocyanate content of from 11.8 to 14.4% by weight, an average isocyanate functionality of from 3.1 to 4.0 and less than about 0.1% by weight of free tolylene diisocyanate.

The present invention also relates to a process for the preparation of such polyisocyanates by the reaction of organic polyhydroxy compounds with excess quantities of tolylene diisocyanate followed by distillation to remove unreacted excess of this starting diisocyanate down to a residue of less than 0.1% by weight. The polyhydroxy compounds used are polyhydroxy polyethers having a molecular weight in the range of from 350 to 500.

The invention also relates to the use of the new polyisocyanates as polyisocyanate components in polyurethane lacquers, in particular in two-component polyurethane lacquers.

The starting materials for the process according to the invention are tolylene diisocyanate and polyether polyols.

Any of the isomers of tolylene diisocyanate may be used but 2,4-tolylene diisocyanate and commercial mixtures thereof in which up to 35% by weight, based on the mixture, of 2,6-tolylene diisocyanate is present are preferred.

The polyether polyols useful in the process of the present invention have a molecular weight, determined from the hydroxyl group content and hydroxyl functionality, of from 350 to 500, preferably from 400 to 470. Polyether triols having a molecular weight within these ranges are preferred. The polyether polyols which may be used in the practice of the present invention may be obtained in known manner by the alkoxylation of suitable starter molecules or suitable mixtures of starter molecules. The preferred compounds used for alkoxylation are propylene oxide and/or ethylene oxide. The alkoxylation may be carried out on mixtures of these starting materials or successively on individual starting materials in any sequence. It is particularly preferred to use the polypropylene oxide polyethers obtained by the propoxylation of trihydric alcohols which are free from ether groups. Glycerol and/or trimethylolpropane are preferred starter molecules.

To carry out the process of the present invention, the polyether polyols are reacted with tolylene diisocyanate at temperatures of from about 40 to about 140° C., preferably at 50 to 110° C. The quantities of the reactants generally corresponds to an NCO/OH equivalent ratio of from about 4:1 to about 20:1, preferably from about 5:1 to about 10:1.

After the prepolymerization, the excess of unreacted tolylene diisocyanate is removed, preferably by vacuum thin layer distillation at from 100 to 180° C., preferably from 120 to 160° C. The polyisocyanates according to the invention are then obtained in the form of semi-rigid resins.

The polyisocyanates of the present invention have a very low melt viscosity compared with the polyisocyanates known in the art. Their viscosity at 100° C. is generally less than about 20,000 mPa.s, preferably less than about 10,000 mPa.s. Due to the low melt viscosity, monomeric diisocyanates can be removed particularly effectively by vacuum thin layer distillation so that the residue of free tolylene diisocyanate can easily be reduced to less than 0.1% by weight in the thin layer evaporators conventionally used in the art.

The polyisocyanates of the present invention are polyisocyanate mixtures whose gel chromatographic analysis shows the simultaneous presence of polyisocyanates having a functionality of 3 as the main component and polyisocyanates of higher functionality as subsidiary components. The average functionality which can be calculated from the isocyanate content and from the molecular weight determined by vapor pressure osmometry is therefore generally in the range of from 3.1 to 4.0, preferably from 3.3 to 3.8.

The polyisocyanates of the present invention are generally used in the form of a solution in an organic solvent. Examples of suitable solvents include the known lacquer solvents such as ethyl acetate, butyl acetate, methoxypropyl acetate, toluene, the isomeric xylenes and commercial solvents such as Solvesso of Exxon Chemicals or mixtures of such solvents. It has surprisingly been shown that solutions of the polyisocyanates according to the invention can be much more easily diluted with odorless aliphatic solvents than solutions known in the art. Examples of such solvents include petroleum ethers, cleaning petrol, light petrol, white spirits and various types of isoparaffinic solvents such as Isopar of Exxon Chemicals. This property is particularly advantageous for use in closed work spaces.

The polyisocyanates of the present invention are valuable raw materials for one-component and two-component polyurethane lacquers. The particularly preferred field of application of the new polyisocyanates is their use as polyisocyanate components in two-component polyurethane lacquers.

The reactants for the polyisocyanates of the present invention for this preferred application are the polyhydroxy polyesters and polyethers known to those skilled in the technology of polyurethane lacquers, polyhydroxy polyacrylates and optionally low molecular weight polyhydric alcohols. Polyamines, particularly those in blocked form as polyketimines or oxazolidines, could also be used as reactants for the production of lacquers from the polyisocyanate of the present invention.

The quantitative ratios in which the polyisocyanates of the present invention and the above-mentioned reactants are used for the preparation of two-component polyurethane lacquers are generally chosen to provide from about 0.8 to about 3 isocyanate reactive groups, preferably from about 0.9 to about 1.1 such groups, for one isocyanate group.

When formulating two-component polyurethane coating compounds from the polyisocyanates of the present invention and polyhydroxy compounds, it was surprisingly found that these systems have a substantially longer pot life than state of the art formulations.

When exceptionally rapid complete hardening is required, the catalysts commonly used in isocyanate chemistry may be added. Specific examples of suitable catalysts include: amines such as triethylamine, pyridine, methyl pyridine, benzyl dimethylamine, N,N'-dimethylpiperazine and metal salts such as iron(III) chloride, zinc chloride, zinc-2-ethylcaproate, tin(II)-2-ethylcaproate, dibutyl tin(IV) dilaurate or molybdenum glycolate.

One-component polyurethane lacquers containing the polyisocyanates of the present invention as binders and two-component polyurethane lacquers containing the polyisocyanates of the present invention as cross-linking agents produce lacquer films which have outstanding abrasion resistance combined with excellent adherence to a wide variety of substrates. In addition, the lacquer films are distinguished by great hardness and elasticity.

The polyurethane lacquers which contain polyisocyanates produced in accordance with the present invention as binders or hardeners may, of course, contain the usual auxiliary agents and additives used in lacquer technology, such as pigments, levelling agents, fillers, and the like.

Having thus described our invention, the following Examples are given as being illustrative thereof. The percentages in these Examples are all percentages by weight.

EXAMPLES

Example 1

Preparation of a polyisocyanate 440 g of a polyether having an average molecular weight of 440 prepared by the propoxylation of trimethylolpropane were slowly added dropwise to 3654 g of a mixture of 80% of 2,4-tolylene diisocyanate and 20% of 2,6-tolylene diisocyanate at 60° C. Stirring was continued for 2 hours at 60° C. after all the polyether had been added. The product was then freed from monomeric diisocyanate by vacuum thin layer distillation at 140° C./0.1 mm. The almost colorless resin obtained had a viscosity of 4700 mPa.s/100° C. The product was dissolved to form an 80% solution in methoxypropyl acetate. The solution had the following characteristics:

| | |
|---|---|
| Solids content: | 80% |
| Viscosity: | 10,500 mPa · s/22° C. |
| NCO content: | 10.5% |
| Molecular weight: | 1150 g/mol (determined by vapor pressure osmometry) |
| Calculated NCO functionality: | 3.59 |
| Monomer content: | 0.03% by weight. |

The solution was diluted with white spirits down to a proportion by weight of 45%.

Example 2

Preparation of a polyisocyanate

Example 1 was repeated with the exception that 440 g of a mixture of 65% of 2,4-tolylene diisocyanate and 35% of 2,6-tolylene diisocyanate were used as the isocyanate. The resulting solvent-free, pale yellow resin had a melt viscosity of 5500 mPa.s/1$\phi$° C. and was dissolved in ethyl acetate to a concentration of 80%. The solution had the following characteristics:

| | |
|---|---|
| Solids content: | 80% |
| Viscosity: | 1500 mPa · s/22° C. |
| NCO content: | 10.3% |
| Molecular weight: | 1160 g/mol (determined by vapor pressure osmometry) |
| Calc. NCO functionality: | 3.57 |
| Monomer content: | 0.03% by weight |

The solution was diluted with white spirits down to a proportion by weight of 50%.

Example 3

Preparation of a polyisocyanate 360 g of a polyether having a molecular weight of 360 prepared by the propoxylation of trimethylolpropane were slowly added dropwise to 4698 g of 2,4-tolylene diisocyanate at 60° C. The product was worked up as in Example 1 after 2 hours of stirring at 60° C. The almost colorless resin obtained had a melt viscosity of 18,400 mPa.s/100° C. The product was dissolved to a concentration of 80% in ethyl acetate. The solution had the following characteristics:

| | |
|---|---|
| Solids content: | 80% |
| Viscosity: | 3700 mPa · s/22° C. |
| NCO content: | 11.2% |
| Molecular weight: | 978 g/mol (determined by vapor pressure osmometry) |
| Calc. NCO functionality: | 3.26 |
| Monomer content: | 0.04% by weight. |

Example 4

Preparation of a polyisocyanate (Comparison Example)

A mixture of 252 g of trimethylolpropane and 120 g of diethylene glycol was slowly added dropwise to 3864 g of a mixture of 65% of 2,4-tolylene diisocyanate and 35% of 2,6-tolylene diisocyanate at 80° C. The product was worked up as in Example 1 after 2 hours of stirring at 80° C.

The pale yellow resin obtained had a viscosity above 400,000 mPa.s/100° C. A 75% solution in ethyl acetate had the following characteristics:

| | |
|---|---|
| Solids content: | 75% |
| Viscosity: | 1400 mPa · s/22° C. |
| NCO content: | 13% |
| Molecular weight: | 787 g/mol (determined by vapor pressure osmometry) |
| Calc. NCO functionality: | 3.25 |
| Monomer content: | 0.23% by weight. |

The solution was diluted with white spirits down to a proportion by weight of 15%.

Example 5 (Use)

The polyisocyanates from Example 2 and Example 4 were each mixed with a commercial polyester polyol (Desmophen® 1300, Trade Product of Bayer AG, OH content 4%) to a total concentration of 50% in ethyl acetate at an NCO/OH ratio of 1:1. The properties of each lacquer are summarized in the Table below.

| | Polyisocyanate Example 2 | Polyisocyanate Example 4 |
|---|---|---|
| Pot life (until gelling occurs) | 5 days | 51 hours |
| Drying (180 μm) | 13 hours | 5.5 hours |
| Outflow time (DIN 4) | | |
| immediately | 14 seconds | 15 seconds |
| 4 h | 14 seconds | 16 seconds |
| 8 h | 15 seconds | 17 seconds |
| 24 h | 19 seconds | 29 seconds |
| 32 h | 20 seconds | 48 seconds |
| Pendulum hardness (after 7 days Room Temp.) | 159 seconds | 174 seconds |
| Solvent attack (after 7 days Room Temp.) | 0/0/0/4 | 0/0/0/3 |

| | Polyisocyanate Example 2 | Polyisocyanate Example 4 |
|---|---|---|
| (toluene, methoxypropyl-acetate, ethyl acetate, acetone) | | |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Polyisocyanates based on a polyhydroxy polyether having a molecular weight of from about 350 to about 500 and tolylene diisocyanate containing ether and urethane groups having
   a) an NCO content of from about 11.8 to about 14.4% by weight,
   b) an average NCO functionality of from about 3.1 to about 4.0 and
   c) a free tolylene diisocyanate content of less than about 0.1% by weight.

2. A process for the preparation of polyisocyanates containing ether groups and urethane groups of claim 1 comprising
   a) reacting an organic polyhydroxy polyether having a molecular weight of from about 350 to about 500 with an excess of tolylene diisocyanate and
   b) distilling the reaction mixture of a) to remove unreacted excess diisocyanate down to a residual diisocyanate content of less than 0.1% by weight.

3. The process of claim 2 in which the polyhydroxy polyether used is a polyether triol having a molecular weight in the range of from 350 to 500.

4. The process of claim 3 in which the polyhydroxy polyether used is a polyether triol having a molecular weight in the range of from 400 to 470 which has been prepared by propoxylating a trihydric alcohol which is free of ether groups.

5. The process of claim 4 in which the tolylene diisocyanate used is 2,4-tolylene diisocyanate or a mixture thereof in which up to 35% by weight, based on the mixture, is 2,6-diisocyanatotoluene.

6. The process of claim 3 in which the tolylene diisocyanate used is 2,4-tolylene diisocyanate or a mixture thereof in which up to 35% by weight, based on the mixture, is 2,6-diisocyanatotoluene.

7. A process for the production of a polyurethane lacquer comprising mixing the polyisocyanate containing urethane groups of claim 1 with a polyhydroxy compound.

8. The process of claim 7 in which the polyisocyanate containing urethane and the polyhydroxy compound are used in quantities such that from about 0.8 to about 3 isocyanate reactive groups are present for each isocyanate group.

* * * * *